United States Patent [19]

Copf et al.

[11] Patent Number: 5,002,579
[45] Date of Patent: Mar. 26, 1991

[54] PROSTHESIS COMPONENT AND METHOD FOR ITS MANUFACTURE

[76] Inventors: Franz Copf, Eberhardstr. 1; Ulrich Holz, Lenbachstr. 56, both of D-7000 Stuttgart 1, Fed. Rep. of Germany; Savo Vesel, Jamova 2, YU-6100 Ljubljana, Yugoslavia

[21] Appl. No.: 49,989

[22] Filed: May 15, 1987

[30] Foreign Application Priority Data

May 16, 1986 [DE] Fed. Rep. of Germany ....... 3616665
Mar. 9, 1987 [DE] Fed. Rep. of Germany ....... 3707518

[51] Int. Cl.$^5$ ............................................. A61F 2/34
[52] U.S. Cl. .......................................... 623/23; 623/16
[58] Field of Search ....................... 623/16, 18, 20, 21, 623/22, 23

[56] References Cited

U.S. PATENT DOCUMENTS 4,530,114 7/1985 Tepic .................................... 623/23

Primary Examiner—David J. Isabella
Attorney, Agent, or Firm—Fred Philpitt

[57] ABSTRACT

An orthopedic prothesis component comprising a joint member and an anchoring member coupled thereto, said anchoring member including a plurality of elongated rod shaped anchoring posts and a support plate having an upper surface for carrying said joint member, and a lower surface configured to abut a resected surface of the bone and being connected to said anchoring posts, each of said anchoring posts containing a plurality of anchoring collars disposed at predetermined intervals along said posts, each of said collars having radial surfaces extending beyond the perimeter of said posts, whereby said collars serve to transfer loads imposed on the anchoring posts to spongiose material that is packed around said posts after the posts are positioned in the skeleton bone cavity.

7 Claims, 9 Drawing Sheets

PROSTHESIS COMPONENT AND METHOD FOR ITS MANUFACTURE

DESCRIPTION

The invention relates to a joint prosthesis component.

Today's normal joint prosthesis components consisting of metal which is compatible with tissue and of synthetic material have in addition to the joint member ensuring the function of the joint, an anchoring component which is introduced into a cleared section of a skeleton bone and is anchored securely there using polymethylmethacrylate (PMMA). For producing a bone cement, further fine grained PMMA is generally added to the PMMA. See in this respect "Encyclopadie Naturwissenschaft und Technik", (Encyclopedia of Natural Science and Technology), Verlag Moderne Industrie, 1979, Key Word: "Knochenzement" (Bone Cement). Although, by using bone cements of this type, it was possible for the first time to attach endoprostheses reliable to skeleton bones, nevertheless the adhesive connection is a drawback because of the very different thermal coefficients of expansion of bone cement and of prosthesis material and because of the shrinkage of the bone cement that takes place as it hardens. Also, because of the chemical nature of the bone cement and its hardening, damage to the tissue may occur and a good anchorage is not guaranteed in all bones.

Now it has been recognized that both from the standpoint of static introduction of force as well as with regard to alternating stress and a healthy bone structure, it is advantageous if one produces a biochemical anchorage between the prosthesis component and the skeleton bone section in question. Spongiose material is substantially completely removed in conventional prosthetics and is replaced by the anchorage section of the prosthesis component that takes up a large volume, and is connected directly by bone cement to the solid outer layer of bone. According to the present invention the transmission of force between the prosthesis component and the spongiose material takes place by using a plurality of rod-like anchoring posts which are arranged on a support wall. A very large contact surface between the prosthesis component and spongiose material is therefore produced which leads to a reduction of local stress.

When using the joint prosthesis component according to the present invention, in order to insert the prosthesis component itself a certain volume of spongiose material must be removed from the bone. However, a quantity of the spongiose material is ground in a grinder and then introduced between the anchoring posts so that in the course of the healing process the various particles of spongiose material grow together and around the anchoring posts.

After the anchoring component has thus "grown in", there is a flow of force from the prosthesis component to the skeleton bone that extends over a very large contact surface because of the spongiose material. After the healing process, a porous structure results which is advantageous with regard to the absorbing of shocks. In contrast, with joint prosthesis components anchored with bone cement, the connecting structure between the prosthesis component and the bone is rigid, so that high stresses can occur in the case of sudden loads. This may thus lead to deformation of the bone, and a loosening of the prosthesis. Once the prosthesis begins to loosen, even small relative movements lead to frictional loads and to a worsened fixing condition. Since, when using the prosthesis component according to the present invention, the connecting structure between the prosthesis and bone includes the living spongiosa, the growing spongiosa can also heal local weak points in the connecting structure.

Since, according to the present invention, the anchoring posts extending away from the support wall of the prosthesis component are orientated in a trabecular manner (they extend along the main force-transmission paths), after healing, in the bone supporting the prosthesis component, one has force-transmission conditions very similar to those in a healthy bone. On the other hand, in a prosthesis anchored by cement, the force-transmission conditions are completely different from those in a healthy bone. Additional difficulties may thus occur in sections of bone located away from the prosthesis component.

The anchoring collars provided according to the present invention on the anchoring posts serve to increase the contact surface between the anchoring component of the prosthesis component and the spongiosa. They also serve as means to prevent relative movement between the anchoring posts and the spongiosa and in addition as means for introducing forces into material in the direction of the trabecular spicules, in which direction the spongiosa is particularly capable of carrying a load.

In the present invention the spongiosa, which has grown after the healing of the prosthesis component to the anchoring posts, is not subject to any local stresses which could lead to permanent damage, but on the contrary, is exposed to such strong stimuli that it re-generates itself continuously as in healthy bones and consequently remains grown dynamically against the anchoring posts.

The present invention ensures that in the restored spongiosa no appreciable local cross sectional reductions of the individual column-like gaps filled with spongiosa between the anchoring posts are maintained and no partial volumes of spongiosa are produced which would be subject to high notch effects.

A prosthesis component of the present invention can be fixed to the skeleton bone using an external retaining member for that period of time during which the particles of spongiosa are growing together and against the anchoring posts.

With the present invention it is possible to penetrate a volume of spongiosa as far as possible with anchoring posts, which is an advantage with regard to the smallest possible local stresses on the spongiosa, in which case the support wall then replaces that part of the compact surfaces which must be removed for creating broad access to the volume of spongiosa.

When introducing a prosthesis component, it may be useful to clear out somewhat less spongiosa at individual points of the bone than was initially provided when planning the operation. With a prosthesis component according to the present invention, the effective outer contour can be quickly modified in such cases, in that a piece of corresponding length is cut with pincers from the self-supporting end sections of the anchoring posts.

With the present invention it is ensured that the anchoring posts form a very strong framework withstanding mechanical stresses. Also, with regard to the production of the prosthesis component by casting, connected anchoring posts are an advantage, since in this way only a few ventilation channels are required.

A prosthesis component according to this invention is well suited to the volume of spongiosa available for implantation at the end of the bone. In this way one obtains a particularly good force distribution. The olive-shaped end piece of the prosthesis component facilitates introduction of the prosthesis into the cleared-out end of the bone under the visual conditions which are generally not very good during the operation.

Also, the present invention provides an advantage with regard to easier introduction of the prosthesis component into the bone. In addition, the through-hole of the end piece provided according to one embodiment of the invention facilitates the removal of the prosthesis component from the mould when the latter is produced by casting in a ceramic mould.

With the present invention it is possible to make the transmission of force between the prosthesis component and the spongiosa more uniform, since one obtains an even larger contact surface between the anchoring posts and the spongiosa.

In a prosthesis component according to this invention, one can provide secondary anchoring posts of small cross section at a distance from the support wall, since when producing the prosthesis component by casting, the liquid prosthesis material can be supplied by way of the primary anchoring posts having the larger cross section. In this way one obtains secondary anchoring posts constructed in a clean manner.

A prosthesis component according to this invention can be regarded as a substantially uniform open-pored structure, which after implantation fills the volume of spongiosa in the end of the bone substantially uniformly, the main force-transmission lines extending exactly as in bone which has grown naturally. Due to the fact that the prosthesis volume is crossed substantially uniformly by anchoring posts, the inside of the cage determined generally by the anchoring posts can be filled simply with spongiosa ground to approximately the same grain size in a grinder, the ground spongiosa also remaining satisfactorily inside the prosthesis component if the grain size is adapted to the average spacing of the anchoring posts. Before the implantation of the prosthesis component, the latter may thus be filled with crushed spongiosa and can be introduced together with the prosthesis component into the end of the bone which has been cleared out. This facilitates the operation considerably and also makes it easier to introduce the prosthesis component from a narrow side of the end of the bone; otherwise difficulties would occur in uniformly filling the entire space located between the anchoring posts with spongiosa material. Therefore, the introduction of the prosthesis component from one narrow side of the end of the bone is particularly advantageous, because the ends of muscles attached to the bone have frequently grown firmly to the broad side of the end of the bone. There is thus no need for the ends of these muscles to be severed when introducing the prosthesis component from the narrow side.

The hereinafter specified dimensions of the anchoring posts have proved advantageous (a) with regard to the transmission of forces between the anchoring posts and the spongiosa on the one hand and (b) with regard to the production of the prosthesis component by casting from biomaterial.

In some bones part of the volume of spongiosa located at the end of the bone is under compression when in use, whereas another part of the volume of spongiosa is under tension. Applications of this type can be taken into account in a particularly satisfactory manner with a prosthesis component according to the present invention, since the anchoring posts support anchoring collars in the form of a truncated cone, which after alignment are each particularly well suited for receiving compressive or tensile loads.

If one produces prosthesis components according to the invention then such arrangements of anchoring posts can be achieved at low cost.

One can proceed in a manner similar to that which is known from the casting of bells.

The present invention makes it possible to take into consideration exactly the shape of that bone which is to be provided with the prosthesis component. The surgeon may thus work with a prosthesis component adapted in an optimum manner for a special case.

The developments of the present invention are of advantage with regard to a simple mechanical derivation of the bone model from standard x-ray pictures of the bone to be provided with the prosthesis component.

With the development of the invention according to one embodiment, it is possible to call up that information regarding the geometry of the bone in question, which one could only ascertain by a large number of additional X-ray pictures, and which in addition would be complicated to evaluate, from a supply of bone shape data stored in a mass memory. As regards the main edge contours the bone model produced thus corresponds exactly to the X-ray pictures taken generally in two directions extending perpendicularly to each other, whereas with regard to the less important details of cross sectional variation of the bone, the computer supplements this information from data available to it.

According to another embodiment, the computer also automatically produces a model for the support wall of the prosthesis component so that this support wall forms a cover closing off the area of spongiosa and forming a flush continuation of the compact surfaces of the bone.

According to another embodiment, the computer additionally produces an anchoring post allocation plan whereby, roughly speaking, a corresponding computer program operates so that it aligns the anchoring posts along trabecular spicules and distributes them substantially equally in planes lying at right angles to these spicules.

The development of the invention according to another embodiment facilitates the transformation of the allocation plan produced in this way into the model, since the bases of the anchoring posts are pre-determined mechanically.

The invention will now be described in detail by means of the embodiments shown in the drawings, in which.

Figure 1:
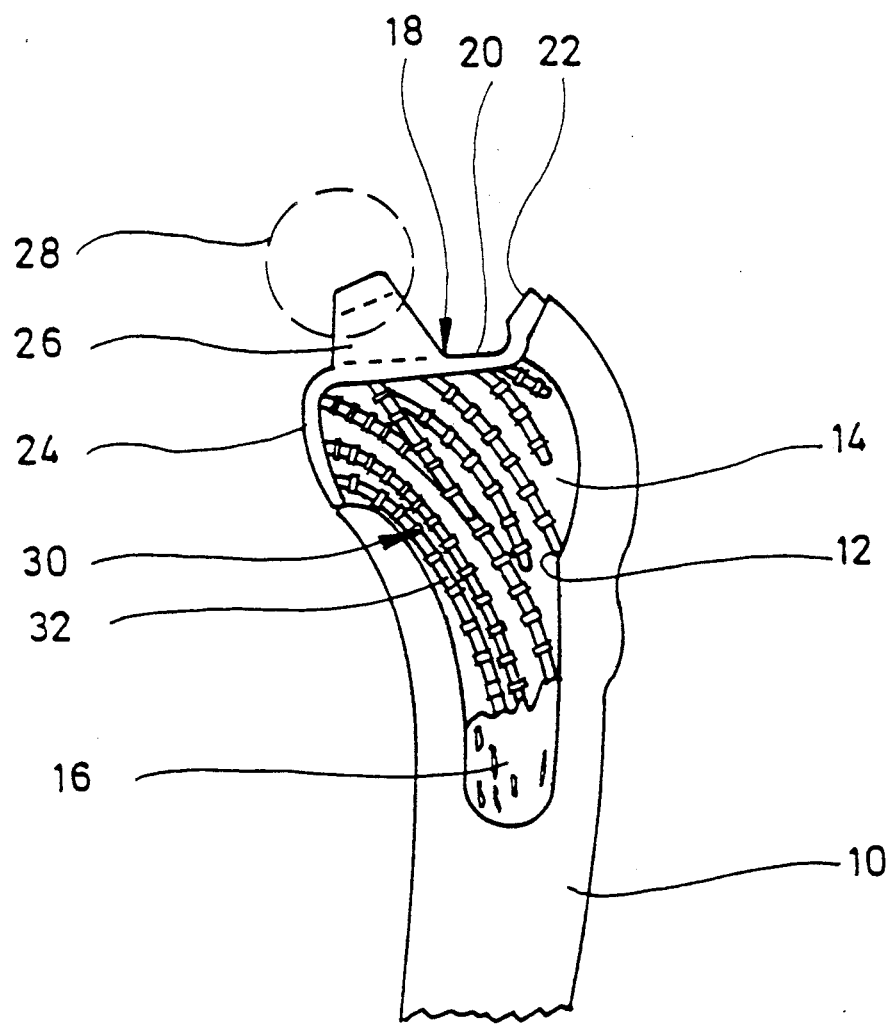
FIG. 1 is a front view of the upper end of a thigh bone with an inserted prosthesis component in a first stage of the insertion process.

FIG. 1 shows an upper end section of a thigh bone 10 which has been prepared for the implantation of a hip joint prosthesis component. For this purpose the joint head and the joint neck have been completely removed and on the front side of the bone, and the solid, compact outer layer (compact surfaces) has been sawed out, so that a window 12 is produced. In the section located behind the window 12 the spongiosa has been cleared out of the thigh bone 10 extensively as far as the compact surface, so that a cavity 14 is created. In FIG. 1, residue of the spongiosa is still visible at 16. At this point one can see the sponge-like cavities.

A prosthesis component designated generally by the reference numeral 18 is introduced into the upper end of the thigh bone 10. The prosthesis component comprises a support wall 20, which substantially has the shape of a double angle, one side 22 of the angle extending towards the lesser trochanter, whereas the second side 24 of the angle forms a flush connection to the Adam's arch. The support wall 20 thus represents a cap, which closes off the upper end of the cavity 14 in a flush manner.

Formed on the upper side of the support wall 20 is a peg 26 to which a joint ball 28 can be attached mechanically as shown by a broken line in FIG. 1. The joint ball cooperates with a joint socket to be implanted in the pelvis, which is not shown in the drawing. The axis of the peg 26 is arranged so that for the joint ball 28 as a whole one obtains a valgus position, thus a position of the joint, which is adjacent to the axis of the shaft of the bone and one obtains the desired ante-torsion angle.

From the inside of the support wall 20 a plurality of attached anchoring posts 30 extend inward into the cavity 14. As shown in the drawing, the fundamental direction in which the anchoring posts 30 extend lines substantially parallel to the axis of the peg 26 and thus in the main load direction (direction of the trabeculae). The individual anchoring posts 30 are somewhat curved to correspond to the path of these trabeculae, in which case parts of these anchoring posts are curved somewhat more steeply in a section adjacent the foot of the posts, so that these anchoring posts can be fixed to the second side 24 of the angle. The free ends of the anchoring posts 30 terminate at a distance from the wall of the cavity 14 consisting of compact surfaces and located on the right in FIG. 1.

As the drawing shows, the anchoring posts 30 each have a plurality of anchoring collars 32 following each other in the axial direction and each comprising a rounded edge.

The anchoring posts 30 are distributed across the cavity 14 at substantially the same distance from each other, so that elongated or column-like gaps having substantially the same cross section remain therebetween.

The annular end faces of the anchoring collars 32, the thickness of the anchoring collars 32, the axial spacing of the anchoring collars 32, the thickness of the core sections of the anchoring posts 30 as well as the length, the number and spacing of the anchoring posts 30 are all designed so that after healing in the prosthesis component of the spongiosa which has grown onto the anchoring posts, the local stresses are not so great that permanent damage to the spongiosa occurs, but on the contrary are not so small that the mechanical stimuli desired for continuous renewal of the spongiosa and smaller disintegration at individual interstices fail to appear.

For this purpose, brief loads should occasionally occur in the spongiosa, which amount to approximately 120% to 140% of the pressure flow limit of the respective type of spongiosa in question. For longer-lasting loads the load may amount to approximately 60% to 80% of the pressure flow limit. For the spongiosa contained in the thigh bone with a pressure flow limit of $2.0 N/mm^2$, this means that a surface pressure of $2.8 N/mm^2$ at maximum should occur at the anchoring collars 32. The annular surface and number of anchoring collars 32 should be chosen accordingly.

As a guide in this respect it can be said that the total surface of the anchoring posts (surfaces of the core sections, end faces and peripheral faces of the anchoring collars) should amount to approximately 130% to approximately 270% of the wall surface of the cavity 14, from which the spongiosa is removed for the implantation of the prosthesis component.

The prosthesis component 18 is an integral casting which is made from a tissue-compatible metal, for example CoCrMo-biomaterial.

Figure 2:
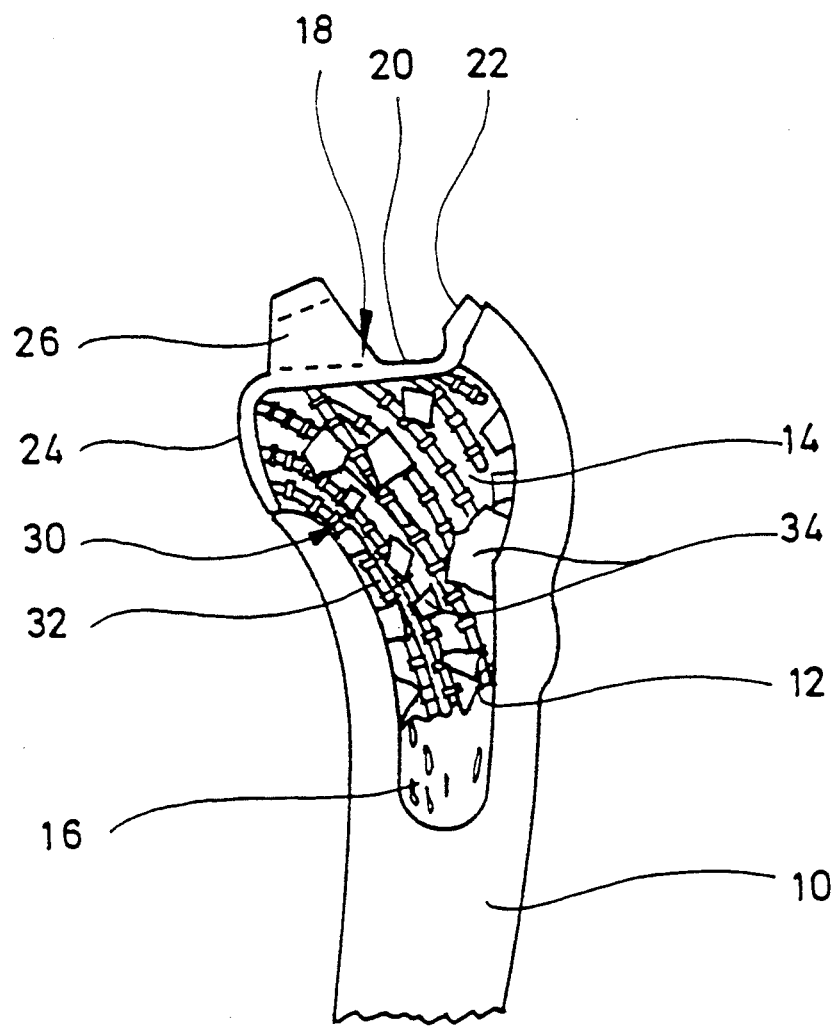
FIG. 2 is a view similar to FIG. 1 in a second stage of the prosthesis implantation.

FIG. 2 shows a second stage of the prosthesis implantation in which the gaps between the anchoring posts 30 are filled with ground spongiosa material, which was previously removed from the bone for forming the cavity 14. For the sake of clearer illustration in FIG. 2, for example, the reference numeral 34 designates somewhat larger spongiosa particles than would be used in practice for the best possible filling of the gaps between the anchoring posts 30.

Figure 3:
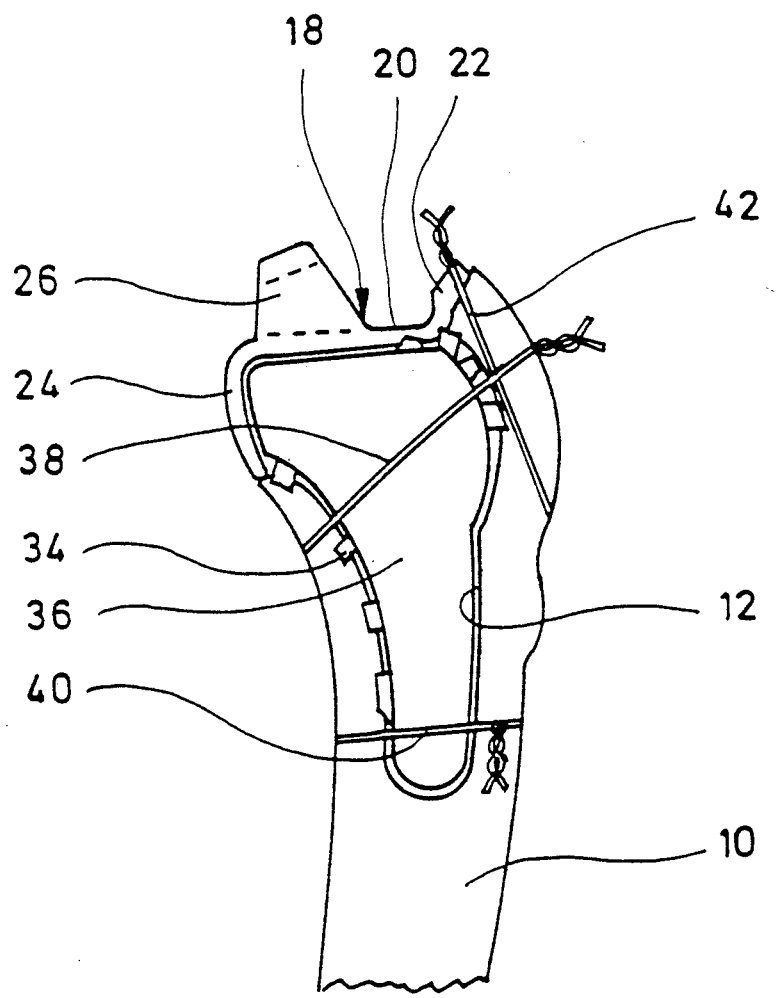
FIG. 3 is a similar view of the thigh bone after completion of implantation and provisional fixing of the prosthesis component.
Figure 4:
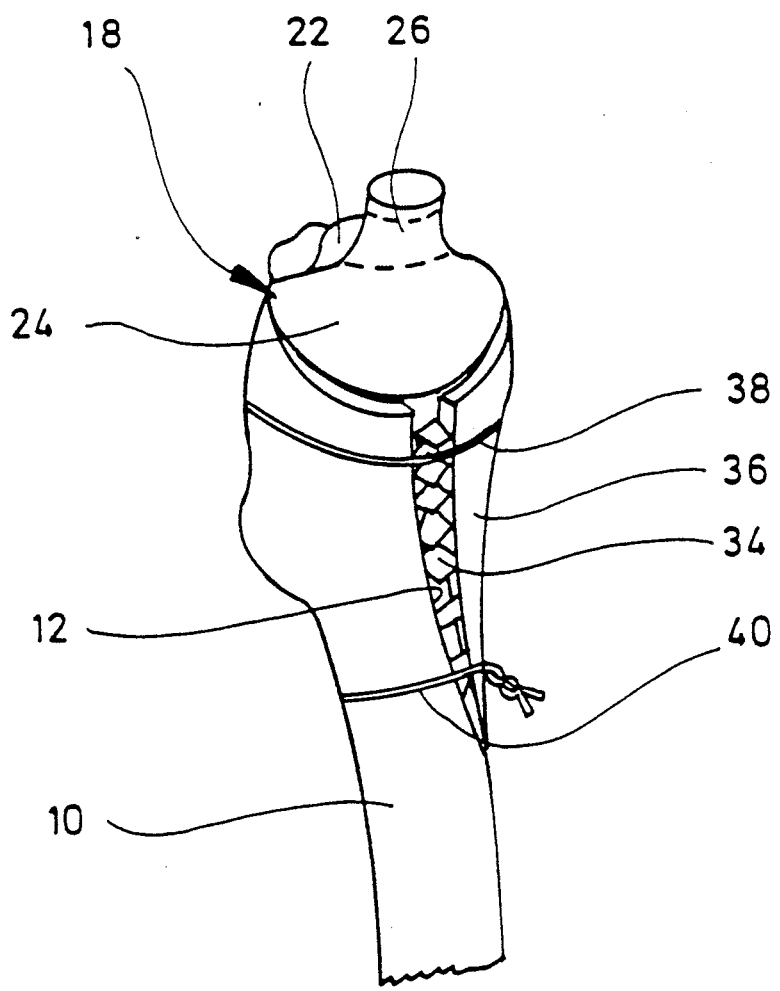
FIG. 4 is a view of the thigh bone after implantation of the prosthesis component in FIG. 3 from the left.
Figure 5:
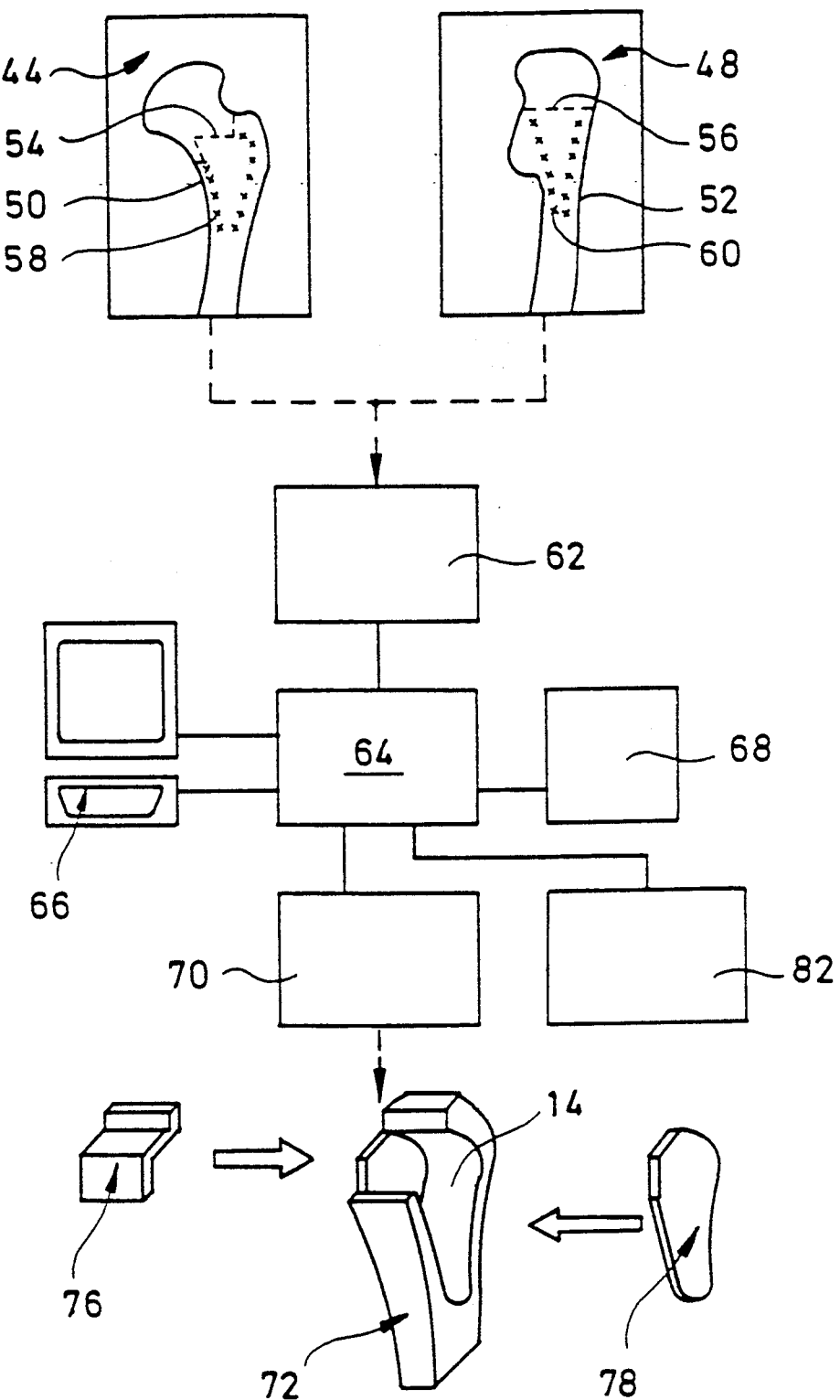
FIG. 5 is a diagrammatic view of an apparatus, which produces a scale model of the bone section to be provided with the prosthesis component.

FIG. 3 shows the thigh bone after filling of the gaps between the anchoring posts 30 with spongiosa particles and after closing the window 12 by the piece 36 of compact material which was previously sawed out. The piece of compact material 36 is fixed in position by two wires, 38 40 of biomaterial. A further wire 42, which is positioned in the channel between the first angle member 22 and the peg 26, serves for temporary fixing of the prosthesis component 18 to the thigh bone until the spongiosa material introduced between the anchoring posts 30 has grown together and has grown against the outer surfaces of the anchoring posts 30. This solidification of the prosthesis component has progressed so far as approximately eight weeks that the prosthesis component 18 is firmly seated. After one year the anchoring posts 30 are surrounded solidly.

When the prosthesis component has grown in solidly the anchoring collars 32 have grown into the spongiosa so that any relative movement between the anchoring posts 30 and the spongiosa is no longer possible in the longitudinal direction of the posts. Since there is a large contact surface between the spongiosa and the anchoring posts, even high static loads can be transmitted reliably from the prosthesis component 18 to the bone, this transfer taking place by way of the spongiosa having a porous structure so that the absorption of shock loads is achieved.

The production of the above-described prosthesis component 18 will be described hereafter with reference to FIGS. 5 to 8.

In order to be able to adapt the geometry of the prosthesis component 18 in an optimum manner for each individual case, the prosthesis component 18 is produced expressly for the specific application. For this purpose one begins with two X-ray pictures 44, 48 which show the upper end of the thigh bone to be provided with the prosthesis component 18 from the front or from the inside of the pelvis. These two pictures of the upper end of the thigh bone, which are perpendicular to each other, already provide quite satisfactory information about the spatial, geometric relationships.

In the two X-ray pictures 44, 48 the edge contour of the bone is defined by aline 50, 52. In addition, the surgeon has marked that line on which he wishes to sever the joint head, by broken lines 54, 56. Lines 58, 60 marked by crosses designate that volume of the upper end section of the bone from which the surgeon intends to remove the spongiosa, in order to create the cavity 14. This space is generally available for the anchoring posts.

The lines 50-60 are fed by way of a digitalizing unit 62 into a programmable computer 64, which cooperates with a display unit 66 and a hard disc memory 68.

At the output side, the computer 64 is connected to a numerically controlled machine tool 70, which mills out from a block of material a 1:1-model of the upper end of the thigh bone, in which the cavity 14 is provided according to scale. This model is reproduced in perspective at 72. For the sake of better understanding it is assumed here that the bone model 72 is derived exclusively from the information which can be taken from the lines 50-60; cross sections through the bone model 72 taken at right angles to the axis of the shaft of the bone are thus substantially rectangular. Where a model of this type is too rough for practice, it can be refined in the manner to be described in more detail hereafter.

In addition to the bone model 72 and controlled by the computer 64, the machine tool 70 produces another model 76 of the support wall 20 of the prosthesis component 18, which represents a cap closing off the upper end of the bone model 72 in a flush manner, and a lateral cover 78, which closes off the cavity 14 and represents a model of the piece 36 of compact material.

Figure 6:
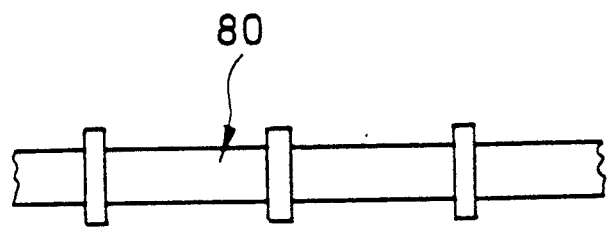
FIG. 6 is a view of a cut-away section from an endless material, such as is used in the production of a prosthesis model.

Starting with the support wall model 76 and the bone model 72, a 1:1-model of the prosthesis component 18 can then be produced, in that the support wall model 76 is equipped with 1:1-models of the anchoring posts 30, which can take place for example starting with the endless material 80 shown to an enlarged scale in FIG. 6. This post model material can be produced in a continuous method, or can also attach individual model rings for the anchoring collars 32 with a press fit or stick them to a corresponding core material.

The computer 64 is also connected at the output side to a plotter 82, which produces an allocation plan for the anchoring posts models in consideration of the cross section of the individual anchoring posts 30, in consideration of the inclination of the peg 26 and in consideration of the desired distance between the anchoring posts 30. This can take place for example in the form of two side views of the model which correspond to the sight lines of the two X-ray pictures 44 and 48. In addition the computer 64 may control the machine tool 70 so that blind holes are drilled in the support wall model 76 at the bases of the postmodels, whereof the inclination corresponds to the pitch of the anchoring posts 30 at the base.

Figure 7:
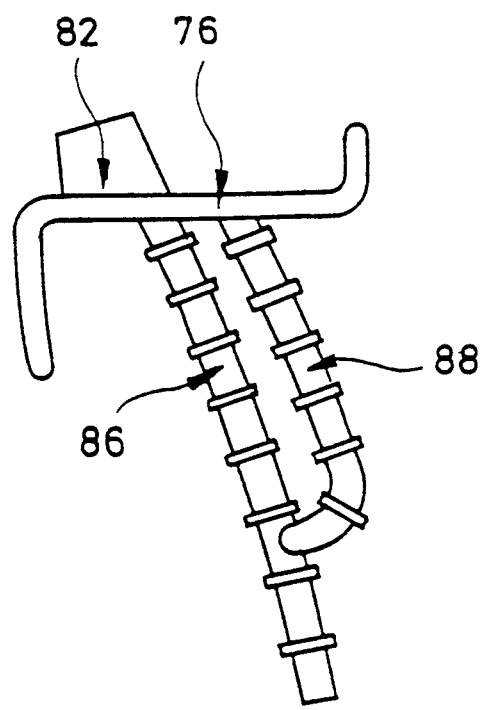
FIG. 7 is a view of a partly finished prosthesis model.

FIG. 7 shows a support wall model 76 on which a peg model 84 is located and which already supports two posts models 86, 88. Further postmodels must still be attached according to the allocation plan produced by the computer by way of the plotter 82.

As shown in FIG. 7, the post models 86, 88 are cut to length from the endless post model material 80 so that the model collars corresponding to the anchoring collars 32 are offset with respect to each other by half a spacing. In this way, notch arrangements closed largely in the peripheral direction are prevented around the spongiosa columns, which later grow between the anchoring posts 30.

In the model shown in FIG. 7, as a modification to the afore-described prosthesis component 28, the post model 88 is bent at its lower end towards the post model 86 and connected to the latter so that one also obtains transverse strengthening in the post bond.

Figure 8:
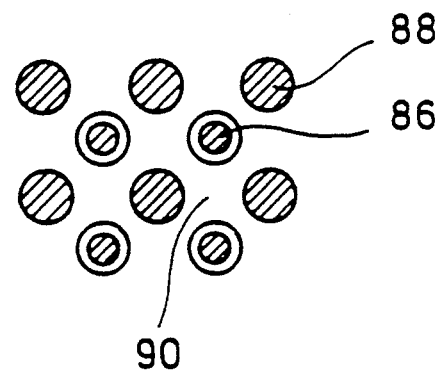
FIG. 8 is a section through the anchoring section of a prosthesis component in a plane extending perpendicularly to the axes of the anchoring posts.

FIG. 8 is a cross section through the post model arrangement from which it can be seen that the various postmodels are uniformly distributed so that gaps 90 having substantially the same cross-sectional surface remain therebetween, which gaps can be filled with spongiosa material. The section plane of FIG. 8 is chosen so that it passes through one set of collars (those of the postmodels 88), whereas the collars of the other set of post models lie outside the plane of the drawing.

The model of the prosthesis component 18 formed by the support wall model 76, the peg model 84 and the various post models 86, 88 is made generally from a material which under a moderate application of heat becomes liquid or volatilizes or decomposes. Then, starting with the prosthesis model, one can produce a negative casting mould due to the fact that one produces a sand mould and after its hardening the model material is removed by a heat treatment. The liquid biomaterial is then poured into the casting mould and after its solidification the casting is removed from the casting mould and cleaned, in which the moulding sand remaining between the anchoring posts is removed thoroughly, for example by sand-blasting. Then, as required, the blank is machined further mechanically, for example burrs are removed. This may be followed by an additional surface treatment, for example polishing and surface coating with titanium.

The above-described manufacturing process can be refined as follows with regard to the production of the bone model:

The three-dimensional geometric data of different characteristic types of thigh bones are stored on the hard disc memory 68, for example in the form of edge contours in sections following each other in the longitudinal direction of the shaft, thus cross sections through the bone. For the different types of bone stored, the computer then checks which type can be best brought by a similarity transformation (linear expansion or compression) into line with the digitalized edge contours of the X-ray pictures 44, 48. This can take place for example in consideration of the mean square deviation between the edge contour lines 50, 52 obtained by digitalization and the corresponding lines of the types of bone stored in the hard disc memory 68. From the type of bone ascertained as being best suited for producing the bone model 72, those data are transferred which facilitate rounding at the edges of the bone model 72. One thus obtains an improved bone model 72, which corresponds in detail to the thigh bone to be provided with the prosthesis component 18.

Figure 9:
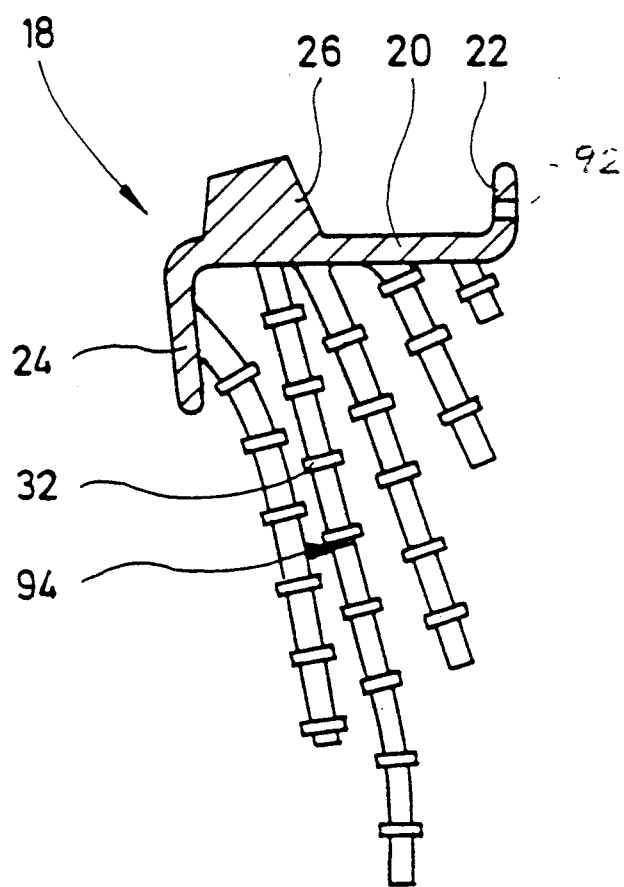
FIG. 9 is a section through the prosthesis component according to FIG. 1 along its central plane.

FIG. 9 is a section through the central plane of the prosthesis component 18, but for the sake of greater clarity only the first anchoring posts located behind the plane of the drawing are illustrated. One can see in the angle member 22 an opening 92 through which the wire serving for tensioning can be drawn, which is in turn fixed in a through hole in the thighbone 20.

In a practical embodiment of a hip joint prosthesis component as described above, the anchoring posts 32 for example may have the following dimensions, if the prosthesis component is cast from CoCrMo-biomaterial:

| | |
|---|---|
| core diameter of the anchoring posts | 2 mm |
| diameter of the anchoring collards | 4 mm |
| axial spacing of the anchoring collars | 6 mm |
| spacing of the anchoring posts in the region in which they extend approximately parallel to each other | 8 mm |
| length of the anchoring collars according to the space available in the cavity 14 (the longest anchoring posts still project into the uppermost part of the bone shaft) | |
| inclination of the anchoring collars at a distance from the foot is approximately according to the inclination of the axis of the peg 26 (longest anchoring posts in the lowermost section are bent towards the axis of the bone shaft (continuation of the longest anchoring posts illustrated in FIG. 1) | |
| thickness of the anchoring collars | 1 mm |

Figure 10:
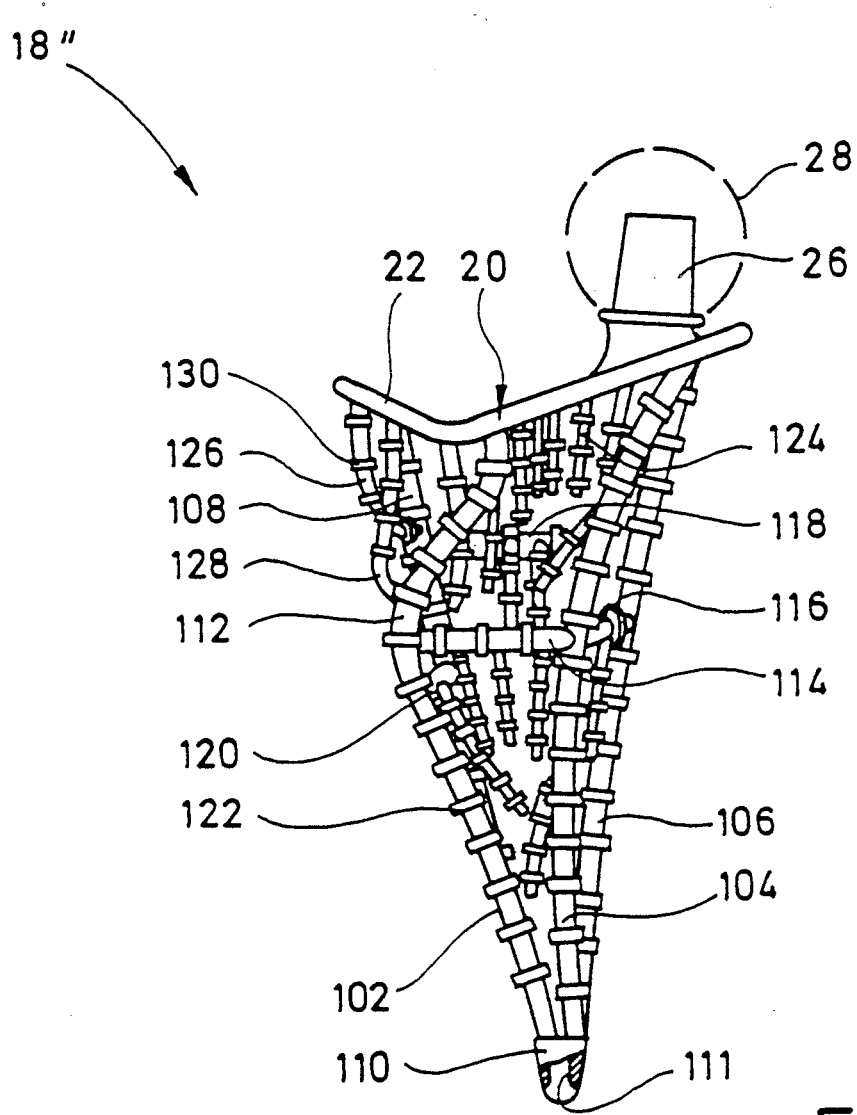
FIG. 10 is a side view of a modified thigh bone prosthesis component.

In the modified joint prosthesis shown in FIG. 10, which is intended for a left thigh bone, parts of the prosthesis which have already been described above, are provided with the same reference numerals.

The bent support wall 20 supports four primary anchoring posts 102, 104, 106 and 108 having a large core diameter, whereof the free ends are cast together with a prosthesis end piece 110, which has substantially the shape of an olive and is smooth on the outside. The primary anchoring posts 102–108 thus form a frame construction which is similar to the Eifel Tower, the individual anchoring posts together forming a cage having a high load-carrying capacity, whereof the transverse cross section decreases from the support wall 20 towards the end piece 110. The individual anchoring posts are swung so that they can fill the spongiosa volume able to be cleared out in the end of the thighbone, virtually up to the edge. Thus, for example, the anchoring posts 106 has a curved post section 112 in order to be able to adapt particularly well to the space filled with spongiosa.

The primary anchoring posts 102–108 extending substantially in the longitudinal direction of the prosthesis are connected by anchoring posts 114, 116, 118 and 120 extending substantially in the peripheral direction and lying at different heights.

In a practical embodiment, the anchoring posts 102–108 and 114–120 each have a core diameter of 3.5 mm, whereas anchoring collars 122 are arranged thereon have an outer diameter of 4.8 mm and follow each other at a distance of 3 mm. The axial dimension of the anchoring collars amounts respectively to approximately 0.6 mm.

Also provided on the support wall 20 are a plurality of secondary anchoring posts 124, which are of short length compared with the primary anchoring posts. In a practical embodiment the length of the secondary anchoring posts 124 amounts to approximately 15–25 mm, the secondary anchoring posts 124 being aligned along trabeculae and some of these secondary anchoring posts 124 being able to have curved sections, as shown at 126, in order that they can be better adapted to the contour of the volume of spongiosa in the end of the bone, and in which case also the ends of some of the secondary anchoring posts 124 can be cast with those of other secondary anchoring posts or with a primary anchoring post, as shown at 128.

In order to be able to fill the part of the framework defined by the primary anchoring posts 102–108, located below the free ends of the secondary anchoring posts 124 carried by the support wall 20, with secondary anchoring posts, one can provide secondary anchoring posts 102–108 or from the thick anchoring posts 114–120 extending in the peripheral direction, in the longitudinal direction of the prosthesis, as illustrated in the drawing.

The prosthesis component illustrated in FIG. 10 thus consists of a cage defining the outer contour and adapted in shape to the volume of spongiosa in the end of the bone, whereof the inside is filled substantially uniformly with secondary anchoring posts 124. In this way one obtains a very large contact surface between the prosthesis component and the regenerated spongiosa which has grown firmly between the primary and secondary anchoring posts after implantation. One thus obtains a very uniform and careful introduction of force into the end of the bone. Since no cement or adhesive is required as in the above-described embodiments, the anchorage of the prosthesis component takes place purely biomechanically and is thus continuously renewed and supplemented, and in the long term a good seating of the prosthesis component is also ensured.

In a practical embodiment of the prosthesis component illustrated in FIG. 1, the secondary anchoring posts have a core diameter of 2.5 mm and an outer diameter of their anchoring collars 130 of 4 mm, the anchoring collards again having a spacing of approximately 3 mm in the longitudinal direction of the posts. Secondary anchoring posts of even smaller dimensions, which could replace part of the secondary anchoring posts 124, have a core diameter of 212 mm, an outer diameter of the anchoring collars of 3 mm and a spacing of the anchor collars of 3 mm. The spacing of these anchoring posts from each other amounts to 6 to 8 mm.

Due to the fact that there are a very large number of secondary anchoring posts, at the same time one also has many retaining possibilities for the ground spongiosa material removed from the end of the bone, which together with the prosthesis component is introduced into the end of the bone and in the latter will again grow together to form a cohesive volume of spongiosa. The prosthesis component illustrated in FIG. 10 can be regarded as a linear sponge, which can retain ground spongiosa satisfactorily between the secondary anchoring posts 124. This makes it possible to introduce the ground spongiosa, prior to implantation of the prosthesis component, between the secondary anchoring posts 124 and thus to introduce the filled prosthesis component into the end of the bone. This way of proceeding does not make it necessary to pack larger quantities of ground spongiosa between the anchoring posts 124 after inserting the prosthesis component and thus one does not need a large access opening to the implantation point. The prosthesis component illustrated in FIG. 10 is thus particularly well suited for insertion from the narrow side of the end of the bone and this makes it possible to carry out the implantation without severing the ends of muscles which have grown onto the broad side of the bone. This can speed up the healing process considerably.

Figure 11:
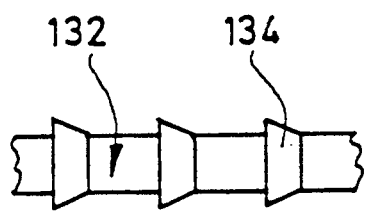
FIGS. 11 to 16 are cut-away views of anchoring posts of modified geometry, to an enlarged scale.

FIG. 11 shows a section of a modified anchoring post 132, which comprises frustoconical anchoring collars 134. An anchoring post of this type can be loaded particularly satisfactorily in that direction in which the forces are aligned with respect to the broad end face of the anchoring collars 134. According to whether in an anchoring post or anchoring post section (it will be understood that an anchoring post may be provided only partly with conical anchoring collars and the remainder with cylindrical anchoring collars, or that one can even provide conical anchoring collars aligned in different ways on a single anchoring post), the broad sides of the anchoring collars point upwards or downwards, the anchoring posts 132 in the prosthesis component may be suitable for receiving compressive loads (broad base surface points upwards) or for receiving tensile loads (broad base surface points downwards).

Figure 12:
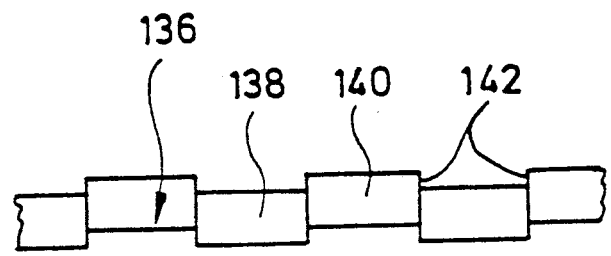

FIG. 12 shows a section of an anchoring post 136 which consists of two sets of cylindrical post sections 138, 140 fitted one in the other, whereof the axes extend parallel to each other at a spaced distance apart. One thus obtains crescent-shaped shoulders 142 which take over the function of the end faces in the shape of a circular ring of the above-described shapes of anchoring collars. The anchoring post 136 is an integral cast or forged part.

Figure 13:
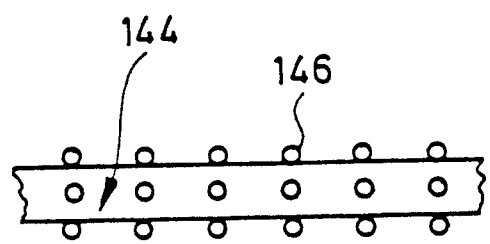

In a further anchoring post 144 according to FIG. 13, anchoring balls 146 are fixed securely, for example cast, onto a smooth core, around which balls the bone material can grow.

Figure 14:
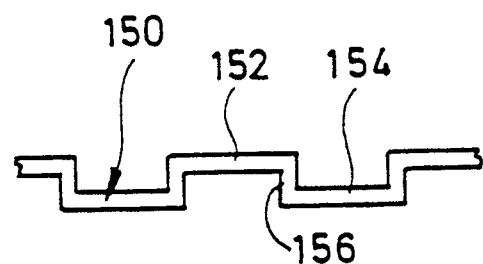

FIG. 14 shows an anchoring post 150 forged for example from titanium with post sections 152 and 154 extending in parallel at a transverse distance, which are connected by transverse post sections 156.

Figure 15:
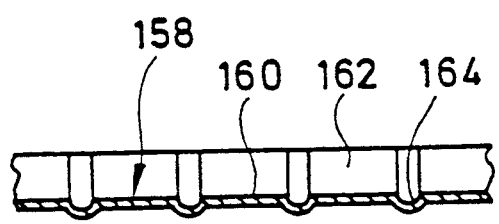

The anchoring post 158 shown in FIG. 15 is a channel-shaped plate-like bending part with a base wall 160 and side walls 162. Crescents 164 extending in the transverse direction are embossed in these walls, which both with their outer side as well as with their inner side present retaining possibilities for the bone material.

Figure 16:
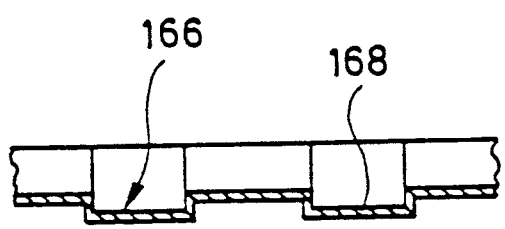

Also, the anchoring post 160 according to FIG. 16 is a channel-shaped plate-like bending part, but which now has a semicircular cross section and into which crescents 168 are pressed, whereof the width corresponds to the spacing of the crescents. The outer surface and inner surface provide shoulders against which the growing bone material can bear.

It is common to the various above-described embodiments of anchoring posts that their axis, or the main direction along which they extend in the prosthesis component, extends along one of the main directions of stress in the bone and that they provide a large number of radial surfaces which prevent an axial relative movement between the anchoring posts and the regenerated bone material growing thereon and respectively transmit a small part of the forces to be transmitted from the prosthesis to the end of the bone as a stimulus to the adjacent volume of spongiosa for natural, continuous regeneration.

The invention has been described above with reference to prosthesis components which are attached as part of a hip joint prosthesis at the upper end of the thigh bone. It will be understood that the invention can be used equally well for other prosthesis components, which are attached to other bones. These are in particular prosthesis components for forming other artificial joints, for example elbow joints, knee joints, finger joints, etc.

We claim:

1. An orthopedic prosthesis component (18) for implantation as a unit into a skeleton bone cavity comprising
    (A) a joint member (29), and
    (B) an anchoring member (20, 30) coupled to said joint member (28), said anchoring member only including:
        (1) a plurality of elongated rod shaped anchoring posts (30) having opposite proximal and distal terminal ends and a substantially cross-sectional perimeter, and
        (2) a support plate (20) having two opposing upper and lower surfaces,
            (a) said upper surface adapted for carrying said joint member (28), and
            (b) said lower surface configured to abut a resected surface of the bone and being connected to said anchoring posts (30) which extend into the prepared bone cavity in a series of curved paths oriented substantially along the trabecular structure of the bone,
    each of said anchoring posts
        containing a plurality of anchoring collars (32) disposed at predetermined intervals intervals along said posts, each of said collars having radial surfaces extending beyond the perimeter of said posts, whereby said collars serve to transfer loads imposed on the anchoring posts to spongiose material that is packed around said posts after the posts are positioned in the skeleton bone cavity.

2. A prosthesis component according to claim 1 wherein at least one anchoring post (88) has said distal end formed with a bend and connected to an adjacent anchoring post (86) at a location thereof which is remote from the distal end of said adjacent anchoring post (86).

3. A prosthesis component according to claim 1 wherein combination of said anchoring posts (102-108) define a tapering outer skeletal surface and wherein the distal ends of each of said anchoring posts of said combination being connected by a rounded end piece (11) that has a substantially smooth outer surface.

4. A prosthesis component according to claim 3 wherein said anchoring posts are divided into a first and second set, said anchoring posts of the first set having a core diameter of about 3.0–4.5 mm and said anchoring posts of the second set having a core diameter of about 1.5–3.0 mm, said anchoring collars of the first set having a diameter of about 0.8–1.5 mm larger than the anchoring posts of the first set and said anchoring collars of the second set having a diameter of about 0.6–2.0 mm larger than the anchoring posts of the second set, and the distance of the intervals between adjacent anchoring collars of the first and second sets being of about 3.0–6.0 mm and 2.0–4.0 mm, respectively.

5. A prosthesis component according to claim 3 wherein the support plate (20) is carried by two sets of anchoring posts, the anchoring posts of the first set being of a first length and a first cross-sectional area, while the anchoring posts of the second set are of a second length and a second cross-sectional area, the second length being smaller than the first length and the second cross-sectional area being smaller than the first cross-sectional area, and in that the anchoring posts of the first set are arranged at a first distance from each other, while the anchoring posts of the second set are arranged at a second distance from each other, the second distance being smaller than the first distance.

6. A prosthesis component according to claim 5 wherein transverse connecting posts (114–120) are formed with anchoring collars, said connecting posts (114–120) connecting the anchoring posts (102–108) of the first set, and in that the connecting posts (114–120) in turn support further anchoring posts (124) of said second length and said second cross-sectional area.

7. A prosthesis component according to claim 5 wherein the anchoring posts (124) of the second set substantially uniformly occupy a volume, the outer contour of which is defined by the anchoring posts (102–108) of the first set.

* * * * *